(12) United States Patent (10) Patent No.: US 7,824,434 B2
von Oepen (45) Date of Patent: Nov. 2, 2010

(54) SELF FORESHORTENING FASTENER

(75) Inventor: Randolf von Oepen, Los Altos Hills, CA (US)

(73) Assignee: DEGIMA GmbH, Pinneberg (DE)

( * ) Notice: Subject to any disclaimer, the term of this patent is extended or adjusted under 35 U.S.C. 154(b) by 475 days.

(21) Appl. No.: 11/146,433

(22) Filed: Jun. 6, 2005

(65) Prior Publication Data

US 2005/0273106 A1 Dec. 8, 2005

Related U.S. Application Data

(60) Provisional application No. 60/577,640, filed on Jun. 7, 2004.

(51) Int. Cl.
*A61B 17/04* (2006.01)
(52) U.S. Cl. ............ 606/313; 606/331; 606/77
(58) Field of Classification Search .......... 606/72, 606/70, 77, 76, 73, 313, 331, 329, 281, 916, 606/104; 411/501; 623/16.11
See application file for complete search history.

(56) References Cited

U.S. PATENT DOCUMENTS

| 5,827,287 | A | 10/1998 | Tunc |
| 5,925,048 | A | 7/1999 | Ahmad et al. |
| 6,206,883 | B1 | 3/2001 | Tunc |
| 6,623,487 | B1 * | 9/2003 | Goshert ............... 606/329 |
| 6,905,501 | B2 | 6/2005 | Nakamura et al. |
| 6,921,402 | B2 * | 7/2005 | Contiliano et al. .......... 606/916 |
| 7,172,593 | B2 * | 2/2007 | Trieu et al. ............ 606/281 |

FOREIGN PATENT DOCUMENTS

WO WO2005/120852 12/2005

OTHER PUBLICATIONS

João F. Mano et al., *Bioinert, biodegradable and injectable polymeric matrix composites for hard tissue replacement: state of the art and recent developments*, Composites Science and Technology 64 (2004) 789-817.
Christiane König et al., *Autosterilization of biodegradable implants by injection molding process*, printed from the website: http://www3.interscience.wiley.com/cgi-bin/abstract/44214/ABSTRACT on May 21, 2005, (2 pages).
C. Mauli Agrawal et al., *Biodegradable polymeric scaffolds for musculoskeletal tissue engineering*, Copyright 2001 John Wiley & Sons, Inc. (10 pages).
U.S. Appl. No. 60/577,640, filed Jun. 7, 2004, von Oepen.

\* cited by examiner

*Primary Examiner*—Pedro Philogene
(74) *Attorney, Agent, or Firm*—Workman Nydegger

(57) ABSTRACT

Disclosed is a fastener that can be mounted to a bone of a patient and can foreshorten and swell of a desired period of time. The fastener can include a head portion and a body portion extending from the head portion. At least one of the head portion and the body portion has a first width that changes to a second width greater than the first width and collectively the head portion and the body portion have a first length that changes to a second length shorter than the first length upon the head portion and the body portion being exposed to a temperature below a glass transition temperature of a polymeric material forming the head portion and the body portion.

22 Claims, 4 Drawing Sheets

SELF FORESHORTENING FASTENER

CROSS-REFERENCE TO RELATED APPLICATIONS

This patent application claims the benefit of U.S. Provisional Patent Application Ser. No. 60/577,640 filed Jun. 7, 2004, and entitled "Self Foreshortening Screw", with Randolf Von Oepen as inventor, the disclosure of which is incorporated herein. Additionally, this United States Patent Application cross-references other United States Patent Applications filed simultaneously herewith on Jun. 6, 2005, entitled "Fastener Having Torque Optimized Head" with Randolf Von Oepen as inventor, and having U.S. patent application Ser. No. 11/145,692, and "Polymeric Plate Bendable Without Thermal Energy and Methods of Manufacture" with Randolf Von Oepen and Alexander Tschakaloff as inventors, and having U.S. patent application Ser. No. 11/146,454. The disclosure of each of the foregoing cross-referenced United States Patent Applications is incorporated herein by reference.

BACKGROUND OF THE INVENTION

1. The Field of the Invention

This application relates generally to fasteners. More specifically, the present invention relates to a medical fastener that can shorten in length and increase in width over time.

2. The Relevant Technology

Bones are a vital skeletal feature and provide the frame and structural support for holding associated muscles and other tissue. Additionally, bones, such as the skull bones and ribs, are responsible for protecting vital organs such as the brain, heart lungs, and the like. While bones are structurally strong, they tend to break for various reasons when subjected to excessive forces. Usually, the healing process includes a medical professional aligning the bones on each side of the break so that the regenerated bone material provides a structurally sound mended bone.

In addition to aligning the bone, various stabilizing techniques have been used to retain the broken bone in proper alignment during the healing process. Traditionally, casts have been used to stabilize minor breaks that do not need structural reinforcement at the bone. On the other hand, some complicated fractures or breaks can be susceptible to falling out of alignment during the healing process. As such, plates and fasteners can be used to stabilize the broken bones or fix bone structures. Use of these kinds of structural reinforcement systems during healing have been known to provide bone regeneration and mending.

Due to excellent strength and stability profiles, metallic fasteners and plates have dominated the market for reinforcing breaks or fractures during healing. The most accepted metallic fasteners and plates are biocompatible titanium and/or titanium alloys; however, other types of metallic materials have also been used. Nevertheless, metallic fasteners and plates can be problematic and have some disadvantages One disadvantage of implanted metallic fasteners and plates arises from being treated as a foreign body, which sometimes requires the fasteners and plates to be removed. This can occur even if the metallic fastener and plate system is initially well tolerated. As such, the subsequent surgery to remove the metallic fastener and plate system can cause additional trauma to the patient, and adds additional costs to the health care system; especially when the patient has to be hospitalized after the procedure. Additionally, if the metallic fastener and plate system includes an iron component, the irons released from the metallic implant may be found in other organs, which can cause long-term problems.

Another major disadvantage of metallic fastener and plate systems arises from being much stronger than the bone being supported. As such, a broken bone that is fixed with a metallic fastener and plate system may not experience proper loading during the healing process. This is because the metallic repair system can carry a large portion of the load that is normally carried by the bone. As a result, the bone can become weaker over time when the metallic repair system is left in place. Accordingly, after removal of the metallic repair system, the repaired bone may be susceptible to fracturing around the region that was previously supported. Even though the metallic repair system provides structural reinforcement to the healing bone, the bone may develop decreased stability.

Additional problems arise because bone is a living structure. When a metallic fastener is drilled into bone, the compact pressure that results, for example, on a plate, is very high and leads to very good initial stability. Under the stress exerted by the fastener and the plate, the bone will change its structure and the fastener may loosen over time. This causes significant problems with maintaining bone alignment during bone regeneration because the plate can move as the fastener loosens.

BRIEF SUMMARY OF THE INVENTION

The present invention overcomes the problems described above by providing a fastener that mounts securely within bone over time. The present invention relates to a biodegradable polymer fastener that foreshortens in length and swells in diameter over time to securely mount within bone.

In one configuration, the fastener includes a head portion and a body portion extending from the head portion. The head portion and the body portion collectively have a first length that changes to a second length shorter than the first length upon the head portion and the body portion being exposed to a body temperature below a glass transition temperature of a polymeric material forming the head portion and the body portion. Alternatively, the polymeric material can have a glass transition temperature that is lower than normal body temperature, but a glass transition temperature higher than the normal body temperature can provide increased stability. The shortening in length can occur before the fastener begins to degrade. Therefore, the width of at least one of the head portion and the body portion can increases in diameter or swell upon the head portion and the body portion being exposed to the temperature below the glass transition temperature of the polymeric material.

According to one aspect, the glass transition temperature is higher than a temperature of a patient's body. For instance, the glass transition temperature can be between about 37 degrees Celsius and about 60 degrees Celsius.

According to another aspect, the polymeric materials can be biodegradable and have a polymer molecule orientation so that the increase in width of at least one of the head portion and the body portion is greater than about 2% after the head portion and said the body portion are immersed within a fluid maintained at about 37 degrees Celsius for 10 days. In other configurations, the increase in width can be from about 3% to about 6% or from about 4% to about 5%.

According to another aspect, the polymeric material forming the fastener can have a polymer molecule orientation that includes less than about 40% of the polymer molecules being oriented in substantially one direction. In another configuration, about 10% to about 30% or the polymer molecules can be oriented in substantially one direction, or about 15% to 25% oriented in substantially one direction.

In another configuration, a method of manufacturing an implantable fastener is provided. The method can include injection molding a biocompatible polymeric composition into a polymeric body within an injection mold cavity of an injection mold. At least a portion of the polymeric body is configured to be an implantable fastener. Following injection molding, the method can include removing the polymeric body from the injection mold, wherein the polymeric body has an amount of polymeric molecules oriented in substantially a first direction so that the polymeric body foreshortens and swells at a temperature below a glass transition temperature of the biocompatible polymeric composition.

The method can also include passing the polymeric composition through an inlet in a master mold that is configured to orientate macromolecules of the biocompatible polymeric composition in substantially a first direction. The inlet can impart a shear stress to the polymeric composition to orientate macromolecules of the biocompatible polymeric composition in substantially the first direction generally parallel to a longitudinal axis of the polymeric body. The inlet can have a cross-sectional length (diameter) from about 10% to about 60% of an average cross-sectional length (diameter) of said injection mold cavity or runner feeding the inlet. In other configurations the inlet diameter or cross-sectional length can range from about 20% to about 50% or from about 30% to about 40% of the mold cavity average cross-sectional length (diameter) or runner cross-sectional length (diameter). As used herein, the term "cross-sectional length" is meant to refer to the diameter of a circular cross-sectional area or width of polygonal cross-sectional area.

According to another aspect, the injection mold can include a master mold and one or more sub-molds. Each of the one or more sub-molds can include the injection mold cavity and the type of sub-mold used with the master mold can be varied based upon the number and type of fastener to be made.

According to another aspect, the method can further include a least one of (i) mixing the polymeric composition in a mixer, (ii) extruding the polymeric composition as a thermoplastic extrudate, (iii) heating the polymeric composition before being introduced into the injection mold cavity, (iv) introducing the polymeric composition into the injection mold cavity under pressure, (v) cooling the polymeric body in the injection mold cavity, (vi) separating the implantable fastener form the polymeric body, or (vii) finishing the implantable fastener.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE EMBODIMENTS

The present invention generally relates to a fastener that mounts tightly and securely within bone as the bone changes its structure under the stress applied by the fastener. The present invention also relates to a fastener made of a biodegradable polymer that shortens in length and swells in diameter to maintain a tight and secure fit within bone during the time when the bone regenerates and degrades following repair of the bone.

Figure 1:
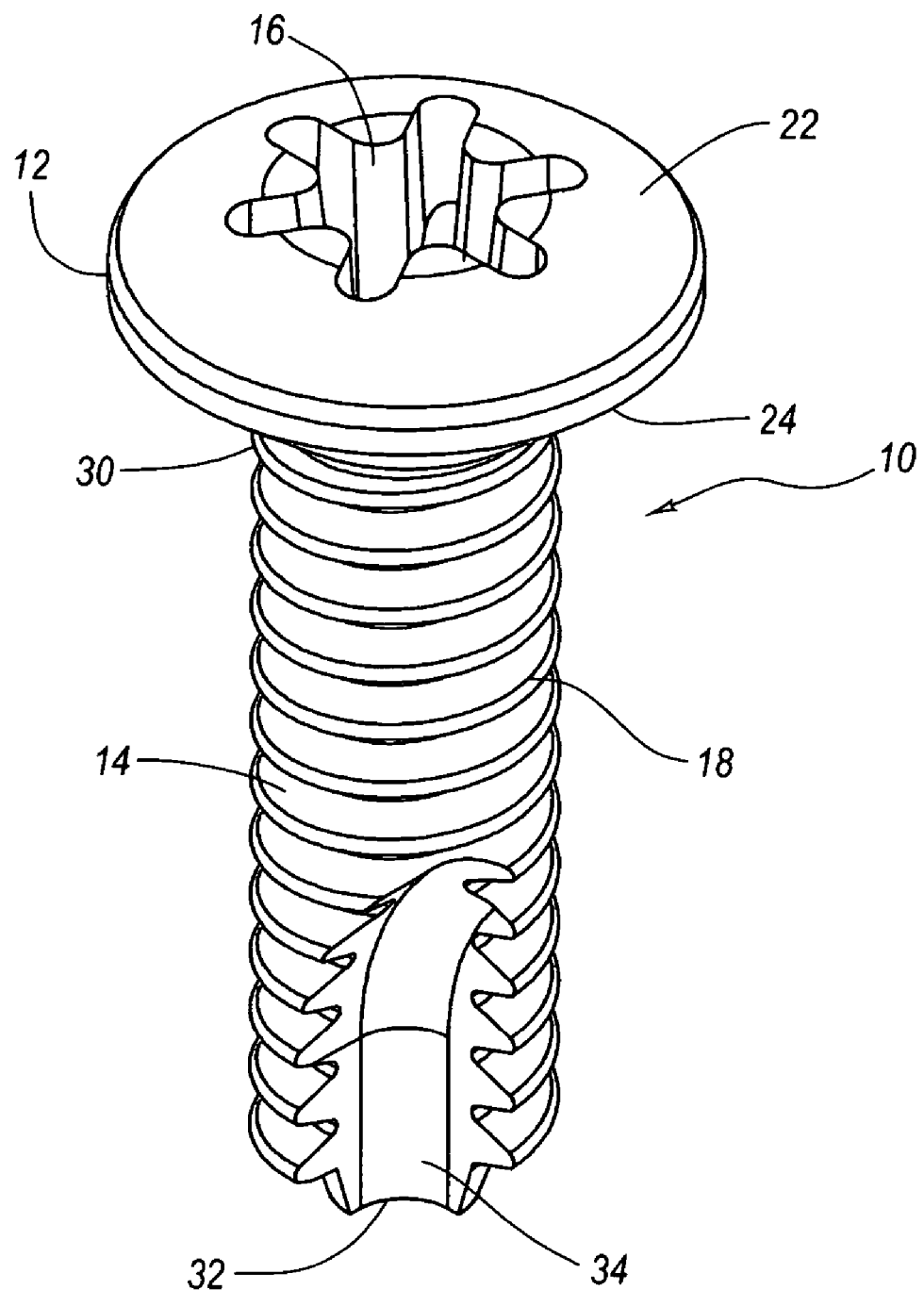
FIG. 1 illustrates a perspective view of a fastener according to the present invention.

Turning to FIG. 1, illustrated is a fastener 10 according to one aspect of the present invention. The fastener 10, such as a screw, pin, bone anchor, suture material, bone pins, meniscus repair systems, clamps or the like, can be used during a medical procedure to aid with positioning bone or fixing other medical devices to patient bone. A driver (not shown) can be used either alone or in combination with an electric drill or other device for rotating the driver to mount the fastener 10 into the bone. Additional information regarding the driver and the manner of mounting the fastener 10 into the bone can be found in co-pending U.S. patent application Ser. No. 11/145,692, entitled "Fastener Having Torque Optimized Head", filed Jun. 6, 2005, which is incorporated herein by this reference.

The illustrated fastener 10 can include a fastener head or head portion 12 and a body portion 14 extending from the head portion 12. The head portion 12 can include a recess 16 to receive the driver (not shown), while a thread 18, such as a raised helical rib, winds around the body portion 14 and can mount or engage with a patient's bone or tissue when the fastener 10 is driven into the bone or tissue. Since the head portion 12 has a diameter greater than the body portion 14, the head portion 12 prevents excessive mounting of the fastener 10 to the bone of a patient, i.e., the head portion 12 prevents the fastener 10 from being driven too deeply into the bone or passing through a mounting hole in a plate mountable to the patient's bone.

With continuing reference to FIG. 1, the head portion 12 can have a curved portion 22 and a generally tapered portion 24. It will be understood, however, that each of the curved portion 22 and the tapered portion 24 can have other configurations. For example either or both of the curved portion 22 and the tapered portion 24 can be planar. Similarly, although the head portion 12 is illustrated as having a generally circular peripheral edge, one skilled in the art can appreciate that the peripheral edge can be polygonal, oval, or any other configuration.

Similarly, while the body portion 14 is illustrated as having a generally uniform cross-section along its length, it will be understood that the body portion 14 can have a tapered configuration or some other configuration so long as the body portion 14 can engage with the patient's bone or other structure within which the fastener 10 is driven. In additional, it will be understood that the head portion 12 and the body portion 14 can have various other configuration that are typically associated with a screw and more generally a threaded fastener, i.e., a fastener including one or more threads to aid in mounting the fastener to a structure.

The thread 18 of the body portion 14 can extend from a first end 30 toward a second tapered end 32. Alternatively, the body portion 14 can extend from a first end 30 to second end 32, wherein the first end and/or the second end can be of a constant dimension or tapered. Interrupting the thread 18 can be a channel 34 having an open end at the second tapered end 32. This channel 34 provides clearance at the end of the fastener 10 to collect particles, such as scale of bone, particles and blood, which are within a hole, optionally tapped, receiving the fastener 10. By collecting the scale of bone, particles and blood, the channel 34 eliminates the possibility that scale of bone, particles and blood can press between the fastener 10 and the hole's wall or threads and prevent the fastener or screw from being driven into the hole. Including the channel 34 can reduce the frictional contact between the fastener 10 and the hole's wall or threads, thereby making it easier to mount the fastener 10 to the patient's bone.

Although the description of the present invention will be directed generally to the shortening and swelling of the fastener 10 for medical procedures, it will be understood by those skilled in the art that the shortening and swelling features of the present invention can apply to other situations and other types of fasteners. Consequently, the presently described invention may be used in other situations outside the medical arts and other types of fasteners.

To alleviate many of the problems associated with existing metallic fasteners, such as the loosening of a metallic fastener in bone over time, the above-described fastener 10 can be manufactured from a biodegradable polymer that foreshortens and swells in diameter over time to maintain a tight and secure fit within bone. The fastener 10 increases in diameter over time to tightly mount to the bone as the stressed bone changes its structure. The fastener 10 can, therefore, maintain desired C, M stability for a period of time longer than existing metallic fasteners or screws. Optionally, the fastener 10 can be manufactured from a polymeric composition comprised of biodegradable, inert, and/or natural polymers.

To achieve the desired foreshortening and swelling, the fastener 10 can be fabricated from a polymer having a high degree of polymer chain orientation, where polymer chain orientation describes the amount of polymer macromolecules that are aligned in one direction. This type of polymer can be referred to as a high orientation polymer. With the polymer being highly orientated, the fastener 10 would be expected to maintain its dimensions when the fastener 10 is exposed to temperatures below its glass transition temperature, or the temperature above which the polymer changes from a hard or brittle condition to a flexible and elastomeric condition. It has been found, however, that when manufactured from a highly orientated polymer the fastener 10 relaxes at temperatures of approximately 37 degrees Celsius (the typically temperature within a patient's body), even if the glass transition temperature is much greater, such as above 50 degrees Celsius or between about 45 degrees Celsius to about 60 degrees Celsius. This relaxing causes the fastener 10 to shorten or shrink in the direction of the orientation of the polymer macromolecules. Aligning the polymer macromolecules with the longitudinal axis of the fastener 10 results in the fastener 10 shortening or shrinking in length. Since the total volume of the fastener 10 remains the same, at least before the fastener 10 begins to biodegrade, the fastener 10 swells as it shortens or shrinks. This swelling maintains the fastener 10 securely within the bone as the bone changes structure under the stress applied by the fastener 10.

The degree of shortening and swelling can be chosen by selecting particular materials and the process used to create the fastener 10. For instance, the fastener 10 can be configured and fabricated to have less than about 6% or 3% shrinkage in length over a period of 10 days after being placed in a 37° C. bath. Alternatively, the fastener 10 can be configured to shrink greater than 2% in length under the same conditions. Moreover, the fastener can swell from about 0.5% to about 10% of an original dimension under the same conditions. It will be understood that other degrees of shrinkage and/or swelling can be appropriate and higher or lower than the identified 3% and 10%.

As described, the shrinkage and/or swelling of the structural element after implantation in a subject can be highly depended on the method of manufacturing, but also of the material. It has been observed that pure amorphous materials have the tendency to shrink more than materials which or by its nature crystalline or semi-crystalline. Thus, amorphous materials can have shrinkage from about 5% to about 50%, or from about 10% to about 30% in other configurations.

Additionally, crystalline or semi-crystalline materials can have a shrink in length from about 0.5% to about 15%, or about 1% to about 10% in other configurations. Accordingly, the swelling in width can be from about 0.5% to about 20%, or from about 1% to about 15% in other configurations. Also, it should be understood that the swelling and foreshortening do not have to be uniform over the width or length of the screw or fastener. Moreover, by varying the dimensions of the fastener (i.e., tapering) the shrinkage and swelling can be adjusted accordingly.

Various types of polymers can be employed in preparing the fastener 10 in accordance with the present invention. The polymers can include a wide range of biocompatible materials that can be implanted within body of a living animal, such as a human, dog, cat, horse, cow, and the like. Additionally, the polymers can be combined and blended in order to achieve compositions that have high initial strengths, shortens and widens over time, and can degrade within a living body over time.

In one embodiment, a polymer composition for use in injection molding the fastener 10 can include at least one biodegradable polymer. For example, the biodegradable polymer composition can include at least one of poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, combinations thereof, or the like. Additionally, these polymers can be used at a wide range of molecular weights, which can range from less than about 25,000 MW to over 1,000,000 MW. More particularly, the molecular weight can vary depending on the type of polymer, initial strength, shortening and swelling rate, degradation rate, and the like. Additional information on the tensile strength, tensile modulus, flexural modulus, and elongations at yield and at break of various biocompatible and biodegradable polymers can be found with Engelberg and Kohn; Physico-mechanical Properties of Degradable Polymers Used in Medical Applications: A Comparative Study; *Biomaterials;* 1991; 12:292-304, which is incorporated herein by reference.

In one embodiment, a polymer composition for use in injection molding the fastener can include at least one inert polymer. For example, the inert polymer can include at least one of high-density polyethylenes, ultra-high-density polyethylenes, low-density polyethylenes, polypropylenes, polyacrylates, polymethylmethacrylates, polyethylmethacrylates, polysulfones, polyetheretherketones, polytetrafluoroethylenes, polyurethanes, polystyrenes, polystyrene-co-butadienes, epoxies, and the like. Such inert polymers can be used at a wide range of molecular weights in order to impart various mechanical strengths and shortening and swelling rate to the fastener 10.

In one embodiment, the polymer composition for use in injection molding a biocompatible fastener 10 can include at least one natural polymer that can be derived from a natural source. Natural polymers can include polysaccharides, proteins, and the like. Examples of some suitable polysaccharides include methylhydroxyethylcellulose, hydroxymethylethylcellulose, carboxymethylcellulose, methylcellulose, ethylcellulose, hydroxyethylcellulose, hydroxyethylpropylcellulose, amylopectin, amylose, seagel, starches, starch acetates, starch hydroxyethyl ethers, ionic starches, long-chain alkylstarches, dextrins, amine starches, phosphate starches, and dialdehyde starches, alginic acid, phycocolloids, agar, gum arabic, guar gum, locust bean gum, gum karaya, gum tragacanth, and the like. Examples of some proteinaceous materials include collagens, caseins, and the like. Moreover, these natural polymers can also impart biodegradable characteristics to the fastener 10.

In one embodiment, the biodegradable polymers can be reinforced with fibers comprised of magnesium, wherein such fibers can significant strength the fastener. For example, short fibers, which are added to the polymer during the injection molding process, can be oriented in the direction of the flow so as to significantly improve the mechanical properties. Additionally, the magnesium fibers can be pretreated with corona plasma or other well-known method to improve the interface between the polymers and fiber. Since pure magnesium can be highly reactive with water or body fluids, the polymer matrix can act as a shield and protect against fast degradation and magnesium reactions. It can also be understood that optionally the fastener can be formed completely from magnesium and subsequently coated with a polymer coating to shield and protect against fast degradation.

In one embodiment, short fibers of biodegradable micro or nano-porous silicon materials, biodegradable ceramics, organic materials can be added to the polymer and fastener. The short fibers, which are added to the polymer during the injection molding process, can be oriented in the direction of the flow and significantly improve the mechanical properties of the resulting fastener. Optionally, these degradable fibers can be pretreated with corona plasma or other well-known method to improve the interface between the polymer matrix and the fiber. Also, the rate of fiber biodegradation can be slowed by being encapsulated within the polymer matrix.

The addition of fibers into the fastener can improve many of the mechanical and/or strength characteristics. In part, this can arise from the nature of the fibers, and/or being oriented with the polymer molecules. For example, the fibers can increase the Young's modulus and increase the strength.

In another embodiment, the fastener can be fabricated from magnesium, biodegradable micro or nano-porous silicon materials, biodegradable ceramics, or organic materials. Optionally, the fastener made from one or more of these materials and ceramics can be coated or covered with a polymer or polymer matrix.

In yet another embodiment, the biodegradable polymers of the fastener can be admixed with a drug for being delivered into the body after implantation. This can include mixing a drug into the polymer composition before being injection molded, or applying a drug-containing polymeric coating onto the fastener. In any event, a portion of the fastener, either the bulk biodegradable polymer or a biodegradable coating can be configured to deliver drugs into the body after being implanted. Accordingly, any drug can be included into the fastener, including but not limited to, analgesics, anti-inflammatory, anti-microbial, and like drugs.

In one embodiment, the biodegradable polymers, inert polymers, natural polymers, magnesium fibers, and/or porous silicon fibers can be prepared into a polymeric blend that is comprised of different types of polymers and materials. As such, a polymeric blend can be configured to achieve injection moldability, polymer molecule orientation, high initial strength, and desired shortening and swelling rates. Moreover, the biodegradable polymers and/or natural polymers can be blended in order to achieve the fastener 10 that can degrade over time after being implanted.

In order to achieve the desired swelling and foreshortening, the polymer molecules can be oriented within the fastener 10 to have a desired amount of orientation. For example, when the polymer is biodegradable, such orientation includes less than about 40% of the polymer molecules oriented in substantially one direction. In other configurations, the orientation can be from about 10% to about 30% oriented in substantially one direction, or from about 15% to 25% oriented in one direction. However, when other polymers or additives are included, variations in the amount of orientation can be achieved and still retain the foreshortening characteristic.

In one embodiment, it can be preferred to prepare the fastener with a biodegradable polymer and another material such as an inert polymer, natural polymer, magnesium fiber, and/or silicon fiber. In one aspect, this can be beneficial to allow biodegradability over time and still retain some structural support after the degradable portion has been depleted. As such, this can be favorable for complex bone reconstructions that may need some long-term support. That is, an initially high amount of support can be provided that decreases over time until a final amount of support is obtained, which allows the bone to reform and strengthen as the biodegradable portion is depleted. Alternatively, additional biodegradable materials can enhance the biodegradability of the fastener. For example, the biodegradable polymer to other material ratio can range from about 10 to about 1, from about 8 to about 4 in other configurations, from about 6 to about 4 in yet other configurations, and vice versa depending on the characteristic desired.

Moreover, an embodiment of the fastener 10 can be configured to shrink in a water bath maintained at about 37° C. As such, the fastener can be configured to have a dimension, such as length, that foreshortens greater than about 1% of its original dimension in a period of 10 days, greater than about 2%, or greater than 4% in other configurations. Additionally, the fastener 10 can be configured to swell in width to be greater than about 2% of its original dimension in a period of 10 days, greater than about 3%, or greater than 5% in other configurations.

In one embodiment, a fabrication system and process can be employed to prepare the fastener 10 (FIG. 1) having features in accordance with the present invention, i.e., impart the desired amount of polymer molecule orientation. Such, a fabrication system can include the use of an injection mold configured to prepare the fastener 10 (FIG. 1) having the characteristics described herein. The injection molding process can impart a shear stress to the polymer molecules that results in the desired amount of orientation, which is usually in the direction of the flow within a mold of the injection molding system. The process of injection molding is a controllable process that results in the fastener 10 (FIG. 1) having the directional molecular orientation to achieve the desired strength and flexibility so that it will not break, fracture, or fatigue during use and will shorten and swell when mounted within bone.

Common elements of an injection molding system can include, but not limited to, the runners, runner network, flow dividers, cold wells, gate regions, gates, and a mold having a mold cavity. By varying the configuration of each of these and manipulating or changing the mold cavity orientation, vents, mold temperature, polymer composition and temperature, and flow or injection rates of an injection mold system the desired amount of polymer molecule orientation can be obtained. For instance, the gate or injection port within the injection mold can be adapted to orient the molecules by the shear stresses that are imparted to the polymeric melt when the injection mold cavity is being filled. A smaller gate can provide a high shear stress and result in high polymer molecule orientation. A cross-sectional length, such as a diameter, of this small gate can be from about 10% to about 60% of the cavity average cross-sectional length (diameter) or runner cross-sectional length (diameter) to provide optimal polymer orientation. In other configurations, the cross-sectional length of the small gate can be from about 12% to about 25%, or from about 15% to about 20%. In still other configurations the small gate diameter or cross-sectional length can range from about 20% to about 50% or from about 30% to about 40% of the mold cavity average cross-sectional length (diameter) or runner cross-sectional length (diameter).

Through optimizing the level of polymeric molecule orientation, the injection molding system can impart mechanical stability to the fastener 10 (FIG. 1), while creating the properties that allow the fastener 10 (FIG. 1) to foreshorten and swell overtime. By optimizing the injection molding conditions (e.g., polymer composition, mold configuration, polymer melt temperature, flow rates, gate configuration, shear stress, etc.), the process can provide the fastener that when implanted in a patient will securely mount to the bone of a patient as it shortens in length and swells in width during the time that the bone changes its structure because of the stress applied by the fastener 10 (FIG. 1).

Figure 2:
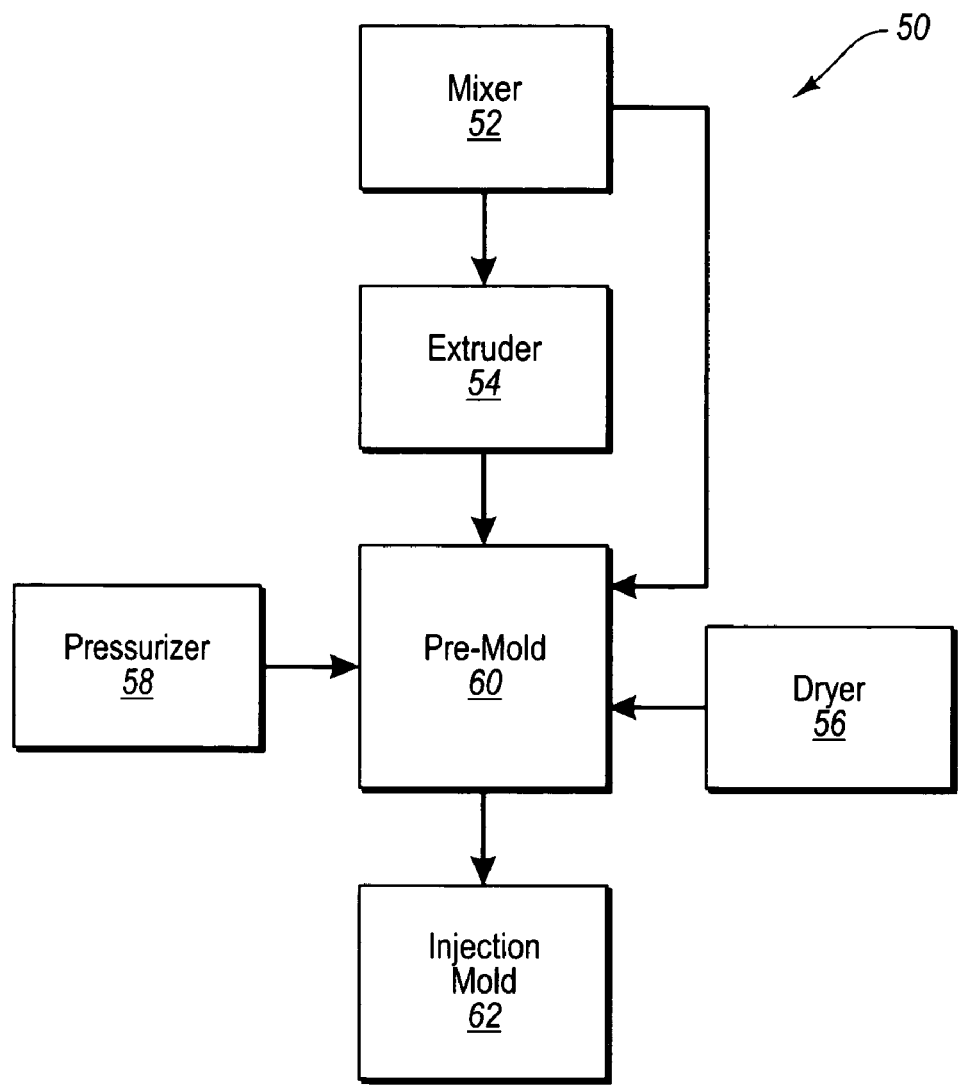
FIG. 2 schematically illustrates one process for manufacturing the fastener according to the present invention.

Turning to FIG. 2, is a schematic diagram illustrating an embodiment of the injection molding system 50 in accordance with the present invention. In general, the injection molding system 50 can be configured to yield an implantable fastener to secure bone or mount a plate to structurally reinforce bone. The injection molding system 50 can include a mixer 52 configured to receive polymeric materials, such as biodegradable and/or inert polymeric materials, in order to form a substantially homogenous polymeric composition. Additionally, the mixer 52 can be configured to receive other types of polymeric materials, plasticizers, rheology-modifying agents, fillers, and the like in order to provide various other characteristics to the fastener 10 (FIG. 1) fabricated with the injection molding system 50.

Optionally, the injection molding system 50 can include an extruder 54. As such, the polymeric composition mixed and formulated within the mixer 52 can be supplied into the extruder 54 for further mixing, compacting, heating, and/or extruding. The extruder 54 can be a single screw extruder, double screw extruder, or piston-type extruder. Additionally, the extruder 54 can include heating elements in order to take advantage of the thermoplastic characteristics of some embodiments of the polymeric composition and heat the composition past its softening point, melting point, and/or glass-transition temperature. In any event, the extruder 54 can extrude the composition through a die head to an extrudate of any shape, which can optionally be pelleted before injection molding.

After being extruded from the extruder 54 or mixed within the mixer 52, the polymeric composition can be introduced into a pre-mold 60. The pre-mold 60 can be a compartment, container, tube, conduit, injection line, or the like in fluid communication with the injection mold 62 that can hold the polymeric material before being injection molded. Alternatively, the composition can be provided directly into the injection mold 62 from the extruder 54 or mixer 52.

Additionally, a dryer 16 can dry the polymeric material while in the pre-mold 20. Sometime the polymeric material can absorb moisture during processing, wherein the moisture can be counter-effective to a resulting plate; especially when a biodegradable polymer, which can cause the plate to prematurely degrade. As such, the dryer 16 can be configured to remove moisture from the polymeric material.

Additionally, a pressurizer 18 can pressurize the pre-mold 20 so that polymeric composition can be injected into the injection mold 22 under high pressure. For example, the injection molding process can be performed at about 10 atm to about 2500 atm or from about 100 atm to about 1500 atm.

The heater 56 and the pressurizer 58 may be optional because the pre-mold 60 and/or the injection mold 62 may be outfitted with such components or otherwise provide these functionalities. In addition to the above, other well-known injection molding equipment may be utilized in conjunction with the pre-mold 60 so as to prepare the polymeric composition for injection molding.

Following heating in the pre-mold 60, the polymeric composition can be injected into the injection mold 62 in order to form the fastener 10 (FIG. 1). For instance, the polymeric composition can be injected into a master mold within a cavity of the injection mold 62, the master mold having one or more cavities that define the configuration of the fastener 10 (FIG. 1). Usually, the process includes injecting the polymeric composition under high pressure and/or heat so that the composition can flow through the various pathways and compartments within the injection mold 62 until it reaches the cavities that define the fastener 10 (FIG. 1).

In the described configuration of the injection molding system 50, the master mold of the injection mold 62 can be cooled by water, air, or fluid flowing through conduits in the master mold or other portions of the injection molding system 50. In this manner, the polymeric composition can be cooled quickly following injection into the master mold so that the orientation of the polymer macromolecules can be fixed and prevented from changing during the molding process.

While general features of the injection molding system 50 have been described in connection with injection molding, various other processes or techniques can be utilized in order to prepare the fastener 10 (FIG. 1) in accordance with the present invention.

Figure 3:
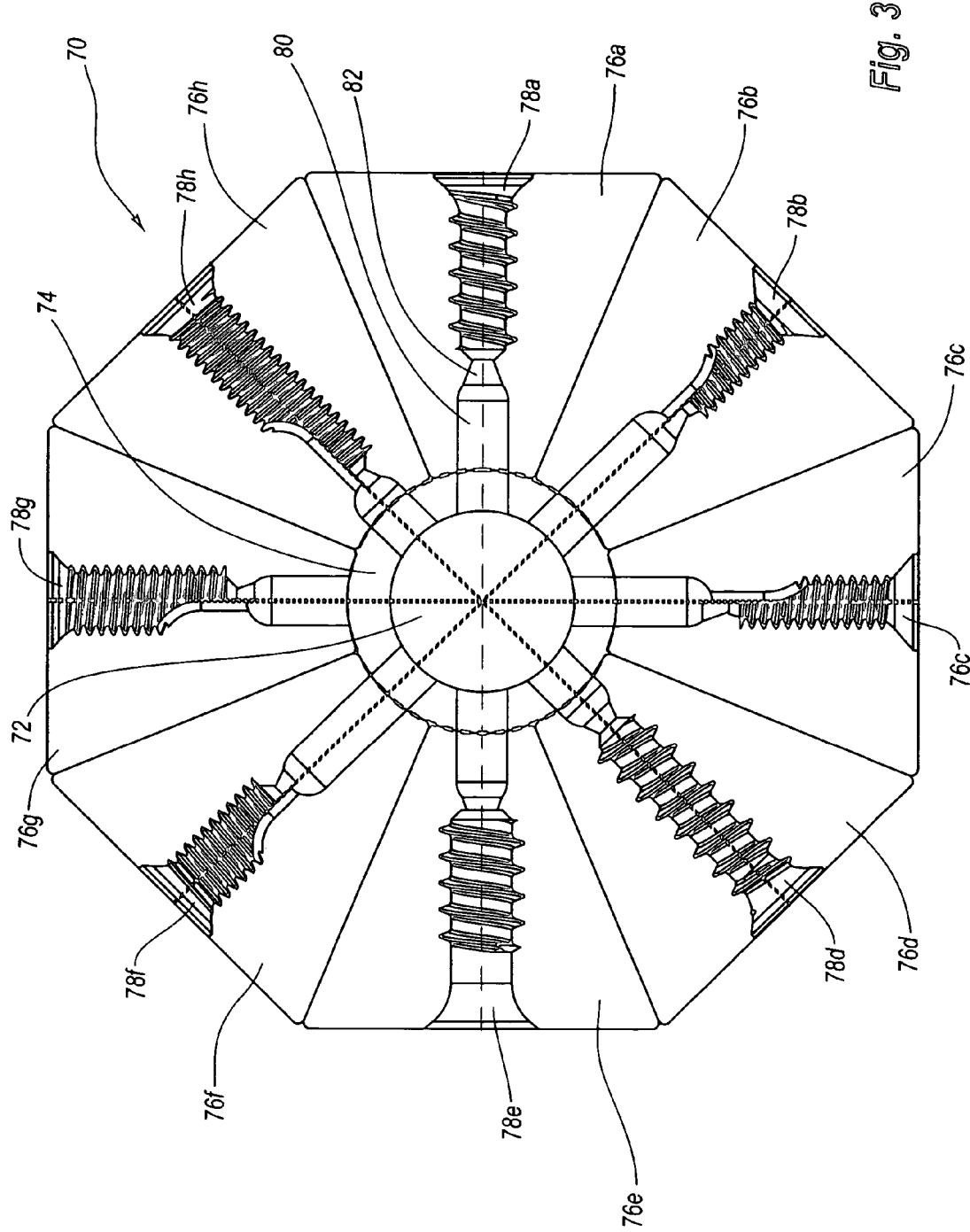
FIG. 3 illustrates one configuration of a master mold usable with the process for manufacturing the fastener of FIG. 2.

Turning to FIG. 3, illustrated is one half of a master mold, identified by reference numeral 70. The following discussion will be directed to the illustrated half, but it will be understood that the discussion also applies to the other half of the master mold since it will have generally a similar or complementary configuration and function. As shown, the master mold 70 has a generally octagonal configuration with a cold runner 74 disposed at its center 72. Spaced around the center 72 are individual sub-molds 76*a*-76*h* that define the configuration of the fastener 10 to be formed using the injection molding system 50 (FIG. 3). Each sub-mold 76*a*-76*h* can include a cavity 78*a*-78*h* that defines the particular configurations of the fastener moldable using that particular sub-mold.

Although the illustrated master mold 70 is illustrated as having eight different sub-molds 76a-76h, it will be understood that in other configurations any combination of sub-molds 76a-76h are possible. For instance, the master mold 70 can include eight or less than eight of any one of the sub-molds 76a-76h.

The following discussion will be directed to the sub-mold 76a. However, a similar discussion can be made with each of the other sub-molds 76b-76h. As illustrated, the sub-mold 76a includes the cavity 78a that communicates with the cold runner 74 by way of a channel 80. A tapered end 82 of the channel 80 provides the inlet to the cavity 78a for the polymer composition. This tapered end 82 acts as a gate having a small diameter to provide a high shear stress to the polymer composition that results in high polymer molecule orientation. Depending upon the particular configuration of the fastener, the tapered end 82 can have a cross-sectional length (diameter) of from about 5% to about 30% of the cavity average cross-sectional length (diameter) or runner cross-sectional length (diameter) to provide optimal polymer orientation. In other configurations, the cross-sectional length (diameter) of the tapered end 82 can be from about 10% to about 25% or from about 15% to about 20% of the cavity average cross-sectional length (diameter) or runner cross-sectional length (diameter). More generally, the cross-sectional area of the tapered end 82 can be sufficiently sized to highly orientate the polymer macromolecules, i.e., apply the level of shear stress to the polymer composition to achieve high polymer molecular orientation. Examples of some cross-sectional shapes for the tapered end 82 can include circles, rectangles, squares, octagons, pentagons, and the like, wherein various polygons can be used in order to provide the proper polymer molecule orientation.

Since the master mold 70 is cooled by water, air, or fluid surrounding and/or passing through conduits in the master mold 70, the high polymer molecule orientation is fixed or frozen during the injection molding process. This results in the fasteners formed by the master mold 70 having the desired high polymer molecule orientation that causes the shorting and swelling of the fastener in the patient's body and below the glass transition temperature.

It will be understood that the injection molding system 50 (FIG. 3) described herein is only one example of a possible injection molding system that can be used to form the fasteners of the present invention. It can be understood that various other types of injection molding system can be used. For instance, the injection molding system 50 (FIG. 3) can include a two body, three body, or multi-body mold, and can be operated with cold or hot runners. Additionally, various modifications can be made to the exemplary mold described herein.

The present invention can also relate to a method of manufacturing the fastener having the features described in accordance with the present invention. Such a method of manufacturing can employ the foregoing compositions, equipment, systems, and processes as previously described. An exemplary method of manufacturing is described in more detail below.

Figure 4:
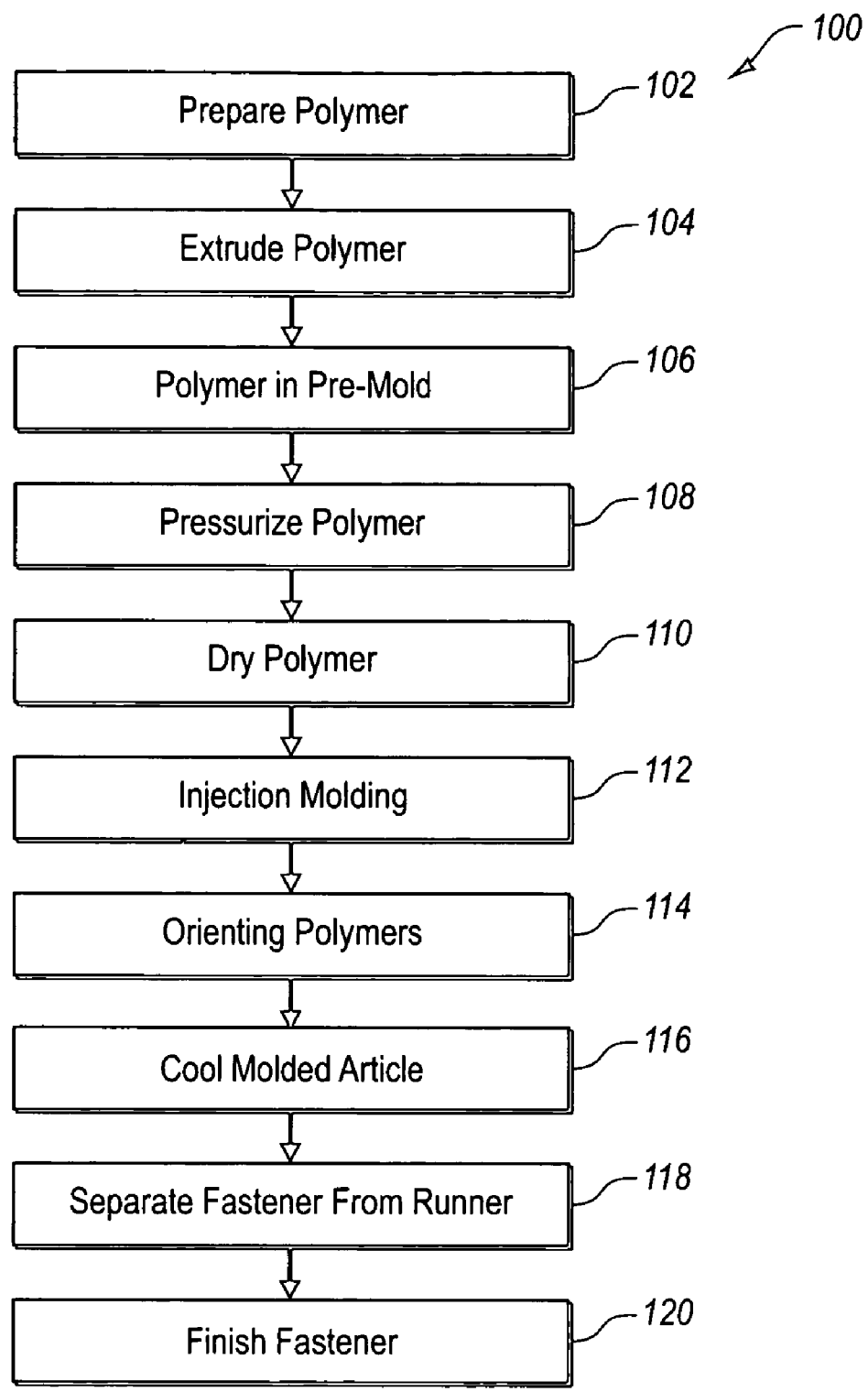
FIG. 4 schematically represents the illustrative methods steps for manufacturing the fastener according to the present invention.

FIG. 4 illustrates an embodiment of an implantable fastener fabrication method 100. Such a fastener fabrication method 100 can include and utilize any of the equipment, components, and processes described in connection to FIG. 1 through FIG. 3 and otherwise know to those in the injection molding art. Accordingly, the fastener fabrication method 100 includes preparing a polymer to have the thermoplastic characteristics and resulting fastener strength and flexibility profiles as described above, as represented by block 102. By preparing the polymer composition to have the proper components and concentrations, the implantable fastener can be prepared to have the preferred foreshortening, swelling, and structural features.

In one embodiment, the polymer composition can be extruded, as represented by block 104. Extruding the polymer composition can be beneficial in order to provide the proper configuration, consistency, temperature, and the like before injection molding. This can include further mixing and/or compaction of the polymeric materials as well as heating the polymer past its softening point, melting point, and/or glass transition temperature.

In any event, the polymer can be supplied into a polymer pre-mold, as represented by block 106. Within the pre-mold, the polymer composition can be pressurized so as to have the proper pressure for being injected into the injection mold, as represented by block 108. Additionally, the polymer composition can be dried in the pre-mold to remove moisture as needed, as represented by block 110.

After being properly conditioned, the polymer composition can be introduced into the injection mold, such as the master mold, for injection molding, as represented by block 112. The polymer molecules in the composition can be oriented by the tapered end 82 (FIG. 3) of the channel 80 leading to the cavity 78 of the master mold 70 to achieve a desired amount of orientation, as represented by block 114. The injection molded body can then be removed from the mold and cooled, as represented by block 116, and the fastener subsequently separated from the polymeric runners or other polymeric features, as represented by block 118. More specifically, when the molded body is formed, which typically includes molded runners, vents, dividers, cold wells, and plate regions, the fastener can be separated from the other features. In any event, the separation can be performed by cutting, pressing, stamping, or otherwise removing the polymer features from the plates.

Moreover, after the fastener has been separated from other polymeric features, the fastener can be finished, as represented by block 120. Finishing can include grinding, surfacing, sanding or otherwise removing anomalies or other surface features on the fastener. Also, the finishing can include providing a coating to the molded fastener, if desired. Additionally, any other well-known process for finishing a molded article can be used in connection herewith in order to substantially finish the fastener into a useable and implantable condition. However, the fastener can be ready for use after injection molding without any further finishing.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A fastener adapted for implanting in bone, the fastener comprising a head portion and a body portion extending from said head portion, said body portion being configured to be driven into and mounted to the bone, said head portion and said body portion collectively having a first length that changes to a second length shorter than said first length and at least one of said head portion and said body portion have a first width that changes to a second width greater than said first width upon said head portion and said body portion being exposed to a moist environment having a temperature below a glass transition temperature of a polymeric material forming said head portion and said body portion following driving said body portion into the bone to mount the fastener to the bone, said change in length and said change in width occurring in response to being placed at a physiological temperature within the bone, the physiological temperature being below the glass transition temperature of the polymeric material used to form said head portion and said body portion.

2. The fastener as recited in claim 1, said length and width changing so as to maintain a tight and secure fit within the bone as the bone heals.

3. The fastener as recited in claim 1, wherein said glass transition temperatures is higher than a temperature of a patient's body.

4. The fastener as recited in claim 1, wherein said glass transition temperatures is between about 37 degrees Celsius and about 60 degrees Celsius.

5. The fastener as recited in claim 1, wherein said polymeric material is a biodegradable polymer.

6. The fastener as recited in claim 1, wherein said polymeric material is highly orientated such that the fastener shortens in length and swells in diameter in response to exposure to a moist environment having a temperature below the glass transition temperature of the polymeric material.

7. A fastener comprising a head portion and a threaded body portion extending from said head portion, said head portion and said threaded body portion collectively having a first width that changes to a second width greater than said first width and a first length that changes to a second length shorter than said first length upon said head portion and said threaded body portion being exposed to a moist environment having a temperature below a glass transition temperature of a biodegradable polymeric material forming said head portion and said threaded body portion, said change in width and said change in length occurring over a period of time following completion of a medical procedure that includes driving said threaded body portion into the bone to mount the fastener to the bone and closure of an incision.

8. The fastener as recited in claim 7, wherein said biodegradable polymeric materials has a polymer molecule orientation so that the increase in width from said first width to said second width is about 3% after said head portion and said threaded body portion are immersed within a fluid maintained at about 37 degrees Celsius for 10 days.

9. The fastener as recited in claim 7, wherein said biodegradable polymeric materials has a polymer molecule orientation that includes less than about 40% of the polymer molecules being oriented in substantially one direction such that the fastener shortens in length and swells in diameter in response to exposure to a moist environment having a temperature below the glass transition temperature of the polymeric material.

10. The fastener as recited in claim 7, wherein said glass transition temperature is higher than a temperature of a patient's body.

11. The fastener as recited in claim 7, wherein said glass transition temperatures is between about 37 degrees Celsius and about 60 degrees Celsius.

12. A fastener adapted for implanting in bone, the fastener comprising a head portion and a body portion extending from said head portion, said head portion and said body portion being reinforced with fibers, said head portion and said body portion collectively having a first length that changes to a second length shorter than said first length and said head portion and said body portion collectively having a first width that changes to a second width greater than said first width upon said head portion and said body portion being exposed to a moist environment having a temperature below a glass transition temperature of a polymeric material forming said head portion and said body portion following driving of said body portion into the bone to mount the fastener to the bone, said change in length and said change in width occurring over a period of time of at least about 10 days in response to being placed at a physiological temperature within the bone, the physiological temperature being below the glass transition temperature of the polymeric material used to form said head portion and said body portion.

13. The fastener as recited in claim 12, wherein said glass transition temperatures is higher than a temperature of a patient's body.

14. The fastener as recited in claim 12, wherein said glass transition temperatures is between about 37 degrees Celsius and about 60 degrees Celsius.

15. The fastener as recited in claim 12, wherein said polymeric material is a biodegradable polymer.

16. The fastener as recited in claim 12, wherein said polymeric material is highly orientated such that the fastener shortens in length and swells in diameter in response to exposure to a moist environment having a temperature below the glass transition temperature of the polymeric material.

17. A fastener that foreshortens in length and swells in diameter over time to securely mount within a bone, the fastener comprising a head portion and a body portion extending from said head portion;
    said body portion being configured to be driven into and mounted to the bone,
    said head portion and said body portion being formed from a polymeric material having a glass transition temperature between about 37 degrees Celsius and about 60 degrees Celsius, said polymeric material being highly oriented such that the fastener is capable of simultaneously shortening in length and swelling in diameter in response to exposure to a moist environment at a physiological temperature;
    said head portion and said body portion collectively having a first length that changes to a second shorter length, said change in length occurring so as to maintain a tight and secure fit within the bone as the bone heals; and
    at least one of said head portion and said body portion having a first diameter that changes to a second greater diameter, said change in diameter occurring so as to maintain a tight and secure fit within the bone as the bone heals,
    said changes in length and diameter occurring over a period of time in response to being placed in the moist environment at the physiological temperature within the bone, the physiological temperature being below the glass transition temperature of the polymeric material used to form said head portion and said body portion.

18. The fastener as recited in claim 17, the physiological temperature being about 37 degrees Celsius.

19. The fastener as recited in claim 17, the period of time being at least 10 days.

20. The fastener as recited in claim 18, the change from the first length to the second length and/or the change in diameter from the first diameter to the second diameter being about 0.5% to about 10% over about 10 days at 37 degrees Celsius.

21. The fastener as recited in claim 18, the change from the first length to the second length and/or the change in diameter from the first diameter to the second diameter being about 2% to about 10% over about 10 days at 37 degrees Celsius.

22. The fastener as recited in claim 18, the change from the first length to the second length and/or the change in diameter from the first diameter to the second diameter being about 3% to about 6% over about 10 days at 37 degrees Celsius.

* * * * *